United States Patent
Daye

(10) Patent No.: US 12,400,615 B2
(45) Date of Patent: Aug. 26, 2025

(54) SYSTEM AND METHOD FOR MEASURING REACTIONS OF A SUBJECT, A COMPUTER PROGRAM AND A COMPUTER-READABLE MEDIUM

(71) Applicant: P³LAB, Céroux-Mousty (BE)

(72) Inventor: Pierre Martin Jack Gérard Daye, Braine-l'alleud (BE)

(73) Assignee: P³LAB, Céroux-Mousty (BE)

( * ) Notice: Subject to any disclaimer, the term of this patent is extended or adjusted under 35 U.S.C. 154(b) by 57 days.

(21) Appl. No.: 18/561,824

(22) PCT Filed: May 19, 2022

(86) PCT No.: PCT/EP2022/063613
§ 371 (c)(1),
(2) Date: Nov. 17, 2023

(87) PCT Pub. No.: WO2022/243454
PCT Pub. Date: Nov. 24, 2022

(65) Prior Publication Data
US 2024/0233671 A1     Jul. 11, 2024

(30) Foreign Application Priority Data
May 19, 2021   (BE) .................................. 2021/5404

(51) Int. Cl.
*G09G 3/36*        (2006.01)
*G06T 7/00*        (2017.01)
(Continued)

(52) U.S. Cl.
CPC ......... *G09G 3/3618* (2013.01); *G06T 7/0012* (2013.01); *A61B 5/163* (2017.08);
(Continued)

(58) Field of Classification Search
CPC ................ G09G 3/3618; G06T 7/0012; G06T 2207/30041; A61B 5/4884; A61B 5/742; A61B 5/163
See application file for complete search history.

(56) References Cited

U.S. PATENT DOCUMENTS 10,748,340 B1 * 8/2020 Zhang ..................... G06F 3/147
11,093,033 B1 * 8/2021 Wang ...................... G06F 3/013
(Continued)

FOREIGN PATENT DOCUMENTS

EP         2358261 A1    8/2011
EP         3064130 A1    9/2016

OTHER PUBLICATIONS

Portengen et al., "Blind spot and visual field anisotropy detection with flicker pupil perimetry across brightness and task variations," Vision Research, Nov. 5, 2020, vol. 178, pp. 79-85, Elsevier, Amsterdam, NL.

(Continued)

*Primary Examiner* — Adam J Snyder
(74) *Attorney, Agent, or Firm* — DICKINSON WRIGHT PLLC

(57) ABSTRACT

The disclosure relates to a system for measuring reactions of a subject, comprising: a screen able to display a plurality of stimuli via a refresh of pixels of the screen, the stimuli being apt to generate reactions from the subject; at least one sensor able to capture images of the subject reacting to the stimuli; and a logic unit configured to command the refresh of the pixels of the screen at a first frequency and the capture of the images of the subject by the sensor at a second frequency, one of the frequencies being an integer multiple of the other frequency. The logic unit also comprises a central clock configured to command the refresh of pixels of the screen and the capture of the images. The disclosure also relates to (Continued)

a method for measuring reactions of a subject, to a computer program and to a computer-readable medium.

20 Claims, 3 Drawing Sheets

(51) Int. Cl.
    *A61B 5/00*     (2006.01)
    *A61B 5/16*     (2006.01)

(52) U.S. Cl.
    CPC ............. *A61B 5/4884* (2013.01); *A61B 5/742* (2013.01); *G06T 2207/30041* (2013.01)

(56) References Cited

U.S. PATENT DOCUMENTS

2015/0297075 A1   10/2015   Klin et al.
2020/0218338 A1*   7/2020   Lee .......................... G06F 3/013

OTHER PUBLICATIONS

International Search Report with Written Opinion and English Translation of PCT Application No. PCT/EP2022/063613, dated Aug. 29, 2022, 15 pages.

* cited by examiner

SYSTEM AND METHOD FOR MEASURING REACTIONS OF A SUBJECT, A COMPUTER PROGRAM AND A COMPUTER-READABLE MEDIUM

CROSS-REFERENCE TO RELATED APPLICATION(S)

This present application is a national stage application of International Patent Application No. PCT/EP2022/063613, filed May 19, 2022, which claims priority to Belgium Patent Application No. 2021/5404, filed May 19, 2021, the disclosures of which are hereby incorporated by reference in their entireties.

TECHNICAL FIELD

The present disclosure relates to a system and a method for measuring reactions of a subject, a computer program and a computer-readable medium.

BACKGROUND

In certain applications, for example in medicine, one wants to track the movement of the eye of a patient ("eye-tracking"); depending on the movement of the eye, which typically reacts to a visual stimulus, one can deduce certain neurological information about the patient.

In general, a screen is used to generate the visual stimulus and "force" the eye to follow or look at a pattern, one or more pixels. One or more cameras capture images of the eye at different times. For example, the document EP2358261 describes a system for presenting stimuli to the eyes of a subject and recording the responses of the pupils. The sequence of stimuli can take the form of a video signal that is displayed on the respective LCD screens at a rate of 60 frames per second. Detectors sample the responses of the pupils in each of the eyes of the subject at a frequency of 30 images per second. One of the frequencies of the screens and of the cameras is twice that of the other, but this document does not indicate how to synchronise the display on the LCD screens and the capture by the detectors. The disadvantage of this technique is that there is a temporal uncertainty between a display of a stimulus by the screens and the capture of images of the eye by the detectors. This uncertainty naturally affects the measurement of the reactions of the subject—particularly ocular reactions—and the processing of the results. This is important when it comes to processing test results, because it has an impact on the complexity of the calculations required to process the results—and therefore on the power and cost of the control unit.

The document Portengeen Brendan L et Al: "Blind spot and visual field anistotropy detection with flicker pupil perimetry across brightness and task validations," Vision Research, Elsevier, Amsterdam, NL, pp. 80-81 (XP086433965) describes the use of the pupil perimeter as a means for measuring the sensitivity across the visual field. An installation is provided comprising a computer on which stimuli are displayed and a camera recording the size of the pupil and the angle of the gaze.

The document EP3064130 describes a device for measuring a subject's reactions. The device comprises a detection system with gaze sensors, a simulation system with a screen positioned in front of the subject's eyes to present him with visual information and a control system with an acquisition unit and a clock. The acquisition unit is configured to receive signals from the stimulation system and signals from the detection system and then to time-stamp these signals with a clock signal from the clock. The time stamping therefore takes place downstream of the acquisition of the signals. The document US20150297075 describes a collection of data related to the display of stimuli and data related to the eyes of a patient. This document describes the association of this acquired data with time-related information. As in the document EP3064130, the time stamping in the document US20150297075 takes place downstream of the acquisition of the signals. Not only do these documents not describe synchronised frequencies, but they also have the disadvantage of having a temporal uncertainty between the display of visual information and the detection by the sensors. As before, this uncertainty naturally affects the measurement of the ocular reactions of the subject and the processing of the results.

There is a need for a system for measuring a subject's reaction to allow to improve the accuracy of measuring the reactions of the subject to stimuli.

BRIEF SUMMARY OF THE DISCLOSURE

One object of the present disclosure is to improve the accuracy of measuring the reactions of the subject to stimuli.

To this end, the disclosure proposes a system for measuring reactions of a subject, comprising:
- a screen capable of displaying a plurality of stimuli via a refresh of pixels of the screen, the stimuli being capable of generating reactions from the subject,
- at least one sensor capable of capturing images of the subject in reaction to the stimuli,
- a logic unit configured to command the refresh of the pixels of the screen at a first frequency and the capture of the images of the subject by the sensor at a second frequency, one of the frequencies being an integer multiple of the other frequency. In addition, the logic unit comprises a central clock configured to command the refresh of pixels of the screen and the capture of the image.

Thanks to the system of the present disclosure, when an image is taken with the system of the disclosure, it is possible to know with certainty which pixel or pixels of the screen have been refreshed. It is possible to determine which refreshed pixel or pixels of the screen displaying the stimuli corresponds to a certain image captured by the sensor. There is therefore a temporal certainty in the correspondence between the data provided by the screen and the sensor, because the same logic unit and the clock it is equipped with command and synchronise the value of the frequencies and the phase of the refresh of the capture. In particular, thanks to the disclosure, the post-processing to match the images of the subject with the appearance of the stimuli is limited, which improves the accuracy of the measurement of the subject's reaction to the stimuli.

According to the particular embodiments, the disclosure may comprise one or more of the following characteristics in any technically possible combination:
- The integer multiple is 1 and the logic unit is configured to command the refresh of the pixels of the screen and the capture of the images of the subject by the sensor at the same frequency.
- The first frequency is faster than the second frequency, the first frequency being an integer multiple of the second frequency.

The second frequency is faster than the first frequency, the second frequency being an integer multiple of the first frequency.

The command of the frequencies for the refresh of the pixels of the screen and for the capture of the images by the sensor is performed solely by the logic unit and the command of the refresh of the pixels of the screen and of the capture of the images by the sensor or the sensors is performed solely by the central clock of the logic unit.

The logic unit is connected directly to the screen and to the sensor.

The images captured by the sensor are images of at least one eye of the subject.

The measurement system comprises two sensors in the form of cameras, each sensor capturing images of a respective eye of the subject.

The at least one sensor and the screen scan from left to right and top to bottom.

The disclosure also relates to a method for measuring a subject's reactions, comprising the following steps:

providing a screen, at least one sensor, and a logic unit comprising a central clock, displaying by the screen a plurality of stimuli by a refresh of pixels of the screen, the stimuli generating reactions from the subject, and capturing by the sensor images of the subject in reaction to the stimuli, the refresh of the pixels of the screen and the capture of the images of the subject by the sensor being commanded by the logic unit at a first frequency and a second frequency respectively, one of the frequencies being an integer multiple of the other frequency. In addition, the central clock is configured to command the refresh of pixels of the screen and the capture of the images by the sensor.

According to the particular embodiments:

the integer multiple is 1, the logic unit commands the refresh of the pixels of the screen and the capture of the images of the subject by the sensor at the same frequency.

the first frequency is faster than the second frequency, the first frequency being an integer multiple of the second frequency.

the second frequency is faster than the first frequency, the second frequency being an integer multiple of the first frequency.

the providing step comprises providing two sensors in the form of cameras.

the capturing step comprises the capture by each sensor of images of a respective eye of the subject.

The disclosure also relates to a computer program comprising instructions which cause the measurement system as described above to execute the steps of the measurement method as described above.

The disclosure also relates to a computer-readable medium on which the computer program described above is recorded.

The embodiments and the advantages of the measurement system according to the disclosure are transposed mutatis mutandis to the measurement method, the computer program and the computer-readable medium according to the disclosure.

Figure 1:
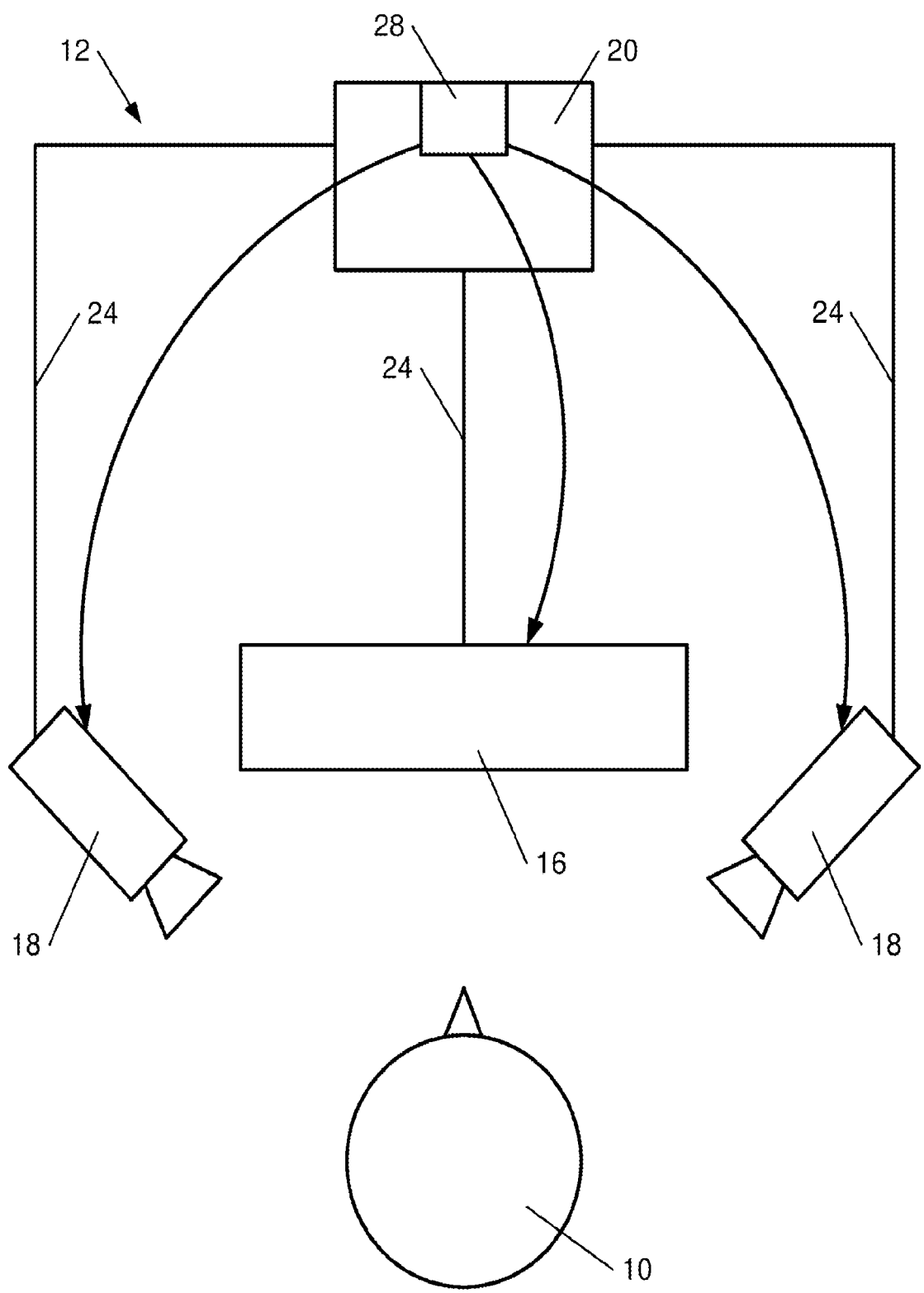
FIG. 1 shows a schematic view of a measurement system according to the invention.

The drawing is not to scale. Similar elements are generally indicated by similar references in the figure. For the purposes of this document, the identical or similar items may have the same references. In addition, the presence of numbers or letters referring to the figure cannot be considered restrictive, even when these numbers or letters are indicated in the claims.

DETAILED DESCRIPTION

This part provides a detailed description of preferred embodiments of the present disclosure. The latter is described with particular embodiments and references to a figure, but the disclosure is not limited thereby. In particular, the figure described below is only schematic and is not limitative.

The use of the verb "comprise", its variants and conjugations in this document in no way precludes the presence of elements other than those mentioned. The use in this document of the indefinite article "a", "an", or the definite article "the" to introduce an element does not exclude the presence of a plurality of these elements.

FIG. 1 illustrates a system 12 for measuring the reaction of a subject 10. The measurement system 12 comprises a screen 16 capable of displaying a plurality of stimuli by a refresh of pixels of the screen 16. The stimuli displayed by the screen 16 are capable of generating reactions from the subject 10. The reactions of the subject 10 are physical reactions, in particular of his face and in particular the reactions of at least one eye of the subject 10. The reactions of the subject 10 may comprise, for example, the movement of his pupil or the increase or the decrease in size of his pupil. The measurement system 12 also comprises at least one sensor 18 capable of capturing images of the subject 10 in reaction to the stimuli. The measurement system 12 also comprises a logic unit 20 configured to command the refresh of the pixels of the screen 16 at a first frequency and the capture of the images of the subject 10 by the sensor 18 at a second frequency. One of the frequencies is an integer multiple of the other frequency. As images of the subject 10 are captured by the sensor or sensors 18 at a frequency that is an integer multiple of the refresh rate of the pixels on the screen 16 (or vice versa), the system allows to obtain an integer number of images captured by the sensor or sensors 18.

The logic unit 20 also comprises a central clock 28 configured to command the refresh of the pixels of the screen 16 and the capture of the images by the sensor 18. In other words, the central clock 28 is configured to command the triggering of the refresh of the pixels of the screen 16 and the capture of the images by the sensor 18. In other words, the central clock 28 is configured to trigger the refresh of the pixels of the screen 16 and the capture of the images by the sensor 18. By using the same clock (a single clock), the refresh of the pixels of the screen 16 and the capture of the images by the sensors 18 are triggered (or activated) at the same time. The rising edges of the clock are used to ensure that the presentation of the first pixel of the screen begins at the same time as the capture by the sensor (and therefore, for example, at the same time as the capture of the first pixel of the first image from the sensor in the form of a camera). In addition, as a result of the command (i.e., the triggering) by the clock 28, the refresh of the pixels of the screen 16 and the capture of the images by the sensors 18 are time-stamped as soon as they are commanded (before they are commanded). They are given time information as soon as they are commanded. One therefore obtains a time information associated with the refresh of the pixels of the screen 16 and with the capture of the images by the sensor or sensors 18, which is triggered at the same time for the refresh and the capture. The triggering of the refresh of the pixels of the screen 16 and of the capture of the images by the sensor 18 is under the exclusive command of the central clock 28, as illustrated by the arrows in FIG. 1. The sensor 18 is only able to capture images once the central clock 28, which commands the triggering of the refresh of the pixels of the screen 16, is activated. In addition, the frequency of the clock 28 corresponds to an integer multiple of the frequency of the screen and of the sensor or sensors. This ensures that the presentation of the first pixel of the second image of the stimulus begins exactly at a rising edge of the clock and that the temporal relationship between the acquisition of the pixels by the sensors and the presentation of the visual stimuli by the screen is preserved.

Thus, on the one hand, the logic unit 20 commands the first and second frequencies applicable to the refresh of the pixels of the screen 16 and to the capture of the images of the subject 10 by the sensor or sensors 18 and, on the other hand, the logic unit 20 comprises the central clock 28 triggering the refresh of pixels of the screen 16 and the capture of the images. The logic unit 20 and the clock 28 therefore synchronise the value of the frequencies applied and the phase of the triggering of the refresh of the pixels of the screen 16 and the capture of the images by the sensor or sensors 18. One obtains a bijective relationship between the moment an image is captured by the sensor or the sensors and a pixel of the screen is displayed, refreshed. This means that measurements of the reactions of the subject can be better coordinated with the display of the stimuli, thereby reducing the computing power required to process the results. This improves the accuracy of the measurement of the reactions of the subject and therefore simplifies the calculations. The system 12 thus allows to avoid any temporal uncertainty between the display of a stimulus on the screen and the capture of images of the eye by the sensor or the sensors. In other words, the system allows to link an image of the subject—the eye, for example—with a given display of stimuli on the screen. The refresh and the capture at respective frequencies that are an integer multiple of each other, and the command (or the command of the triggering) of the refresh and of the capture by the same clock, allows to avoid a desynchronization between the operation of the screen and of the sensor or the sensors, which in turn allows to reduce the computing power required to process the information. This increases the quality of the reaction measurements of the subject.

This architecture allows a temporal alignment between the recordings and the presentation of the stimuli on the screen, because the actions are triggered at the same time and the frequencies are multiple. This allows a precise synchronisation, making it easier to analyse the results. The user will not have to rely on external probes or software tricks to align the stimuli and the recordings. As a result, even if the screen, for example, has a lower frequency, the system gives accurate measurements of the movement times of the eyes (for example, the latency in relation to a change in target position). The display and the acquisition are coordinated in time.

In one embodiment, the integer multiple may be 1; the logic unit 20 is configured to command the refresh of the pixels of the screen 16 and the capture of the images of the subject 10 by the sensor 18 at the same frequency. The first frequency and the second frequency are the same. The refresh command and the command of the capture of the images are then simultaneous. This further allows to reduce the computing power required to process the information.

In another embodiment, one or other of the first and second frequencies is faster than the other, with the faster frequency being an integer multiple of the other frequency. This allows to have a screen or a sensor that is less powerful and therefore less expensive, while still allowing the information to be processed easily. For example, the first frequency of the refresh of the pixels of the screen is faster than the second frequency of capture of the images of the sensor, the first frequency being an integer multiple of the second frequency. Alternatively, the second frequency of capture of the images by the sensor is faster than the first frequency of refresh of the pixels of the screen, the second frequency being an integer multiple of the first frequency. This allows to multiply the images of the subject's reactions in order to obtain more accurate measurements.

The integer multiple n between the two frequencies is chosen from the group {1, 2, 3, 4, 5, 6, 7, 8, 9, 10, 11, 12, etc.}. For a value of 1, the two frequencies are the same. For example, the pixels of the screen 16 are refreshed at a first frequency of between 50 Hz and 500 Hz. By way of example, assuming the second image capture frequency is faster than the first frequency of refresh of the pixels of the screen, the first frequency may be 50 or 60 Hz, the second frequency 500 or 720 Hz respectively and the integer multiple n of 10 or 12 respectively; assuming the first frequency of refresh of the pixels of the screen is faster than the second image capture frequency, the first frequency may be 360 Hz, the second frequency 40 Hz and the integer multiple n of 9.

The screen 16 has a broad meaning in the present application. In one embodiment, the screen 16 is a display device capable of emitting light itself, for example an LED screen. In another embodiment, the screen 16 is a surface capable of reflecting light projected onto the surface, for example light projected by an overhead projector. Preferably, the screen 16 is refreshed by scanning. This allows the pixel refresh information to be controlled and makes it easier to process the results. In particular, the scan is from left to right and top to bottom.

The sensor or sensors 18 are typically a camera. The camera operates in the wavelengths of visible light and/or infrared light and/or ultraviolet light. The camera is provided with pixels to capture images. The images are captured as a video stream by the camera. The images captured by the sensor 18 are in particular images of at least one eye of the subject 10. According to an embodiment shown in FIG. 1, the measurement system 12 comprises several sensors, preferably two sensors 18 in the form of cameras, capturing images at the same second frequency. Each sensor 18 captures images of a respective eye of the subject 10. The presence of two cameras means that one camera can be focused on each eye, increasing the spatial resolution. In another embodiment, the measurement system 12 comprises a single sensor 18, for example also in the form of camera. The single sensor 18 is able to capture the images of two eyes of the subject 10 at the second frequency. Preferably, the capture by the sensor or the sensors 18 is by scanning. This allows to control the capture information and makes it easier to process the results. In particular, the scan is from left to right and top to bottom. The capture by scanning, and from left to right and top to bottom, is particularly applicable to the sensor or sensors in the form of camera.

The refresh of the pixels of the screen 16 and the capture of the images of the subject 10 by the sensor or the sensors 18 at frequencies that are an integer multiple of each other allows to avoid a mismatch between the display of the stimuli on the screen, which would refresh at a first frequency, and the capture of the images by the sensor or the sensors at a second frequency that is not an integer multiple of the first frequency. The system allows to avoid the complex processing of the information.

The logic unit 20 is configured to directly command the refresh of the pixels of the screen 16 and the capture of images of the subject 10 by the sensor or the sensors 18 at a respective frequency, single or integer multiple of each other. The command of the frequencies for refreshing the pixels of the screen 16 and for capturing the images by the sensor 18 is performed solely by the logic unit 20. In other words, the screen 16 itself has no component capable of commanding the refresh frequency of the pixels of the screen 16, and/or the sensor 18 itself has no component capable of commanding the frequency at which images are captured by the sensor 18. Also, the command (of the triggering) of the refresh of the pixels of the screen 16 and/or of the capture of the images by the sensor or the sensors 18 is performed solely by the central clock 28 of the logic unit 20, as illustrated by the arrows in FIG. 1. In other words, the screen 16 and/or the sensor 18 have no clock capable of triggering the refresh of the screen 16 and of the capture of the images by the sensor 18.

In one embodiment, the logic unit 20 is connected directly to the screen 16 and to the sensor 18. In other words, between the logic unit 20 and the screen 16, the measurement system 12 comprises only one cable 24. The measurement system 12 has no component capable of performing a digital processing or a digital command between the logic unit 20 and the screen 16. Between the logic unit 20 and the sensor or the sensors 18, the measurement system 12 comprises only one cable 24. The measurement system 12 has no component capable of performing a digital processing or a digital command between the logic unit 20 and the sensor 18.

The disclosure also relates to a method for measuring the reactions of a subject 10. Firstly, a user provides a screen 16, at least one sensor 18, and a logic unit 20 comprising a central clock 28 as described above. Next, the logic unit 20 commands the refresh of the pixels of the screen 16 and the capture of the images of the subject 10 by the sensor or the sensors 18 at respective frequencies which are an integer multiple of each other. The central clock 28 is also configured to command the refresh of pixels of the screen 16 and the capture of the images by the sensor or the sensors 18. The central clock 28 is configured to command the triggering of pixel refresh of the screen 16 and the capture of the images by the sensor or the sensors 18. The central clock 28 is configured to trigger the pixel refresh of the screen 16 and the capture of the images by the sensor or the sensors 18. The pixel refresh of the screen 16 displays a plurality of stimuli on the screen 16, for example a series of images. The stimuli generate reactions in the subject 10, in particular ocular reactions in the subject 10, for example the movement of the pupil of the subject 10. The sensor 18 captures images of the subject 10 in reaction to the stimuli. The refresh and the capture are at respective frequencies that are an integer multiple of each other and their triggering is commanded by the clock 28. The refresh and the capture have a frequency value and a triggering phase that are synchronised. This allows to reduce the computing power required to process the information and increases the quality of the measurements of the subject's reactions. The logic unit 20 is configured to command the refresh of the pixels of the screen 16 at a first defined frequency, while the images of the subject 10 are captured by the sensor or the sensors 18 at a second frequency, one of the frequencies being an integer multiple of the other frequency.

In one embodiment, the pixels of the screen 16 are refreshed and the images of the subject 10 are captured by the sensor 18 simultaneously at a single frequency. In this way, the images captured by the sensor or the sensors 18 represent the synchronised reaction of the eye to the stimuli presented on the screen 16. The method allows to avoid the need for complex information processing. According to the method, one or other of the first or second frequencies can be the fastest, the fastest frequency being an integer multiple of the slowest frequency.

When the measurement system 12 comprises several sensors, for example two sensors 18, the measurement method comprises the capture by each sensor 18 of images of a respective eye of the subject 10 at a second identical frequency between the plurality of sensors.

Figure 2:
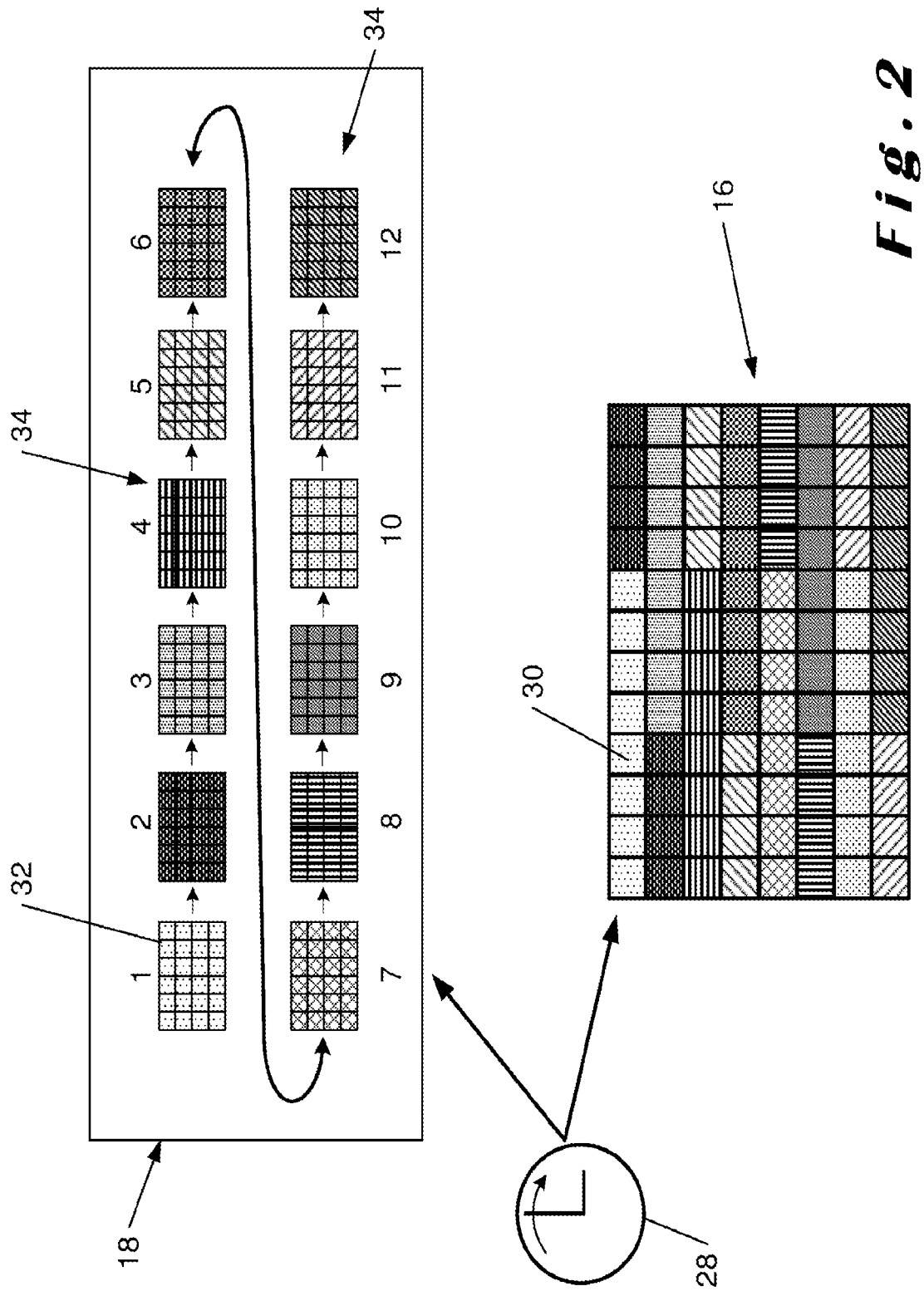
FIG. 2 illustrates a schematic view of the operation of the system according to the invention in one example.
Figure 3:
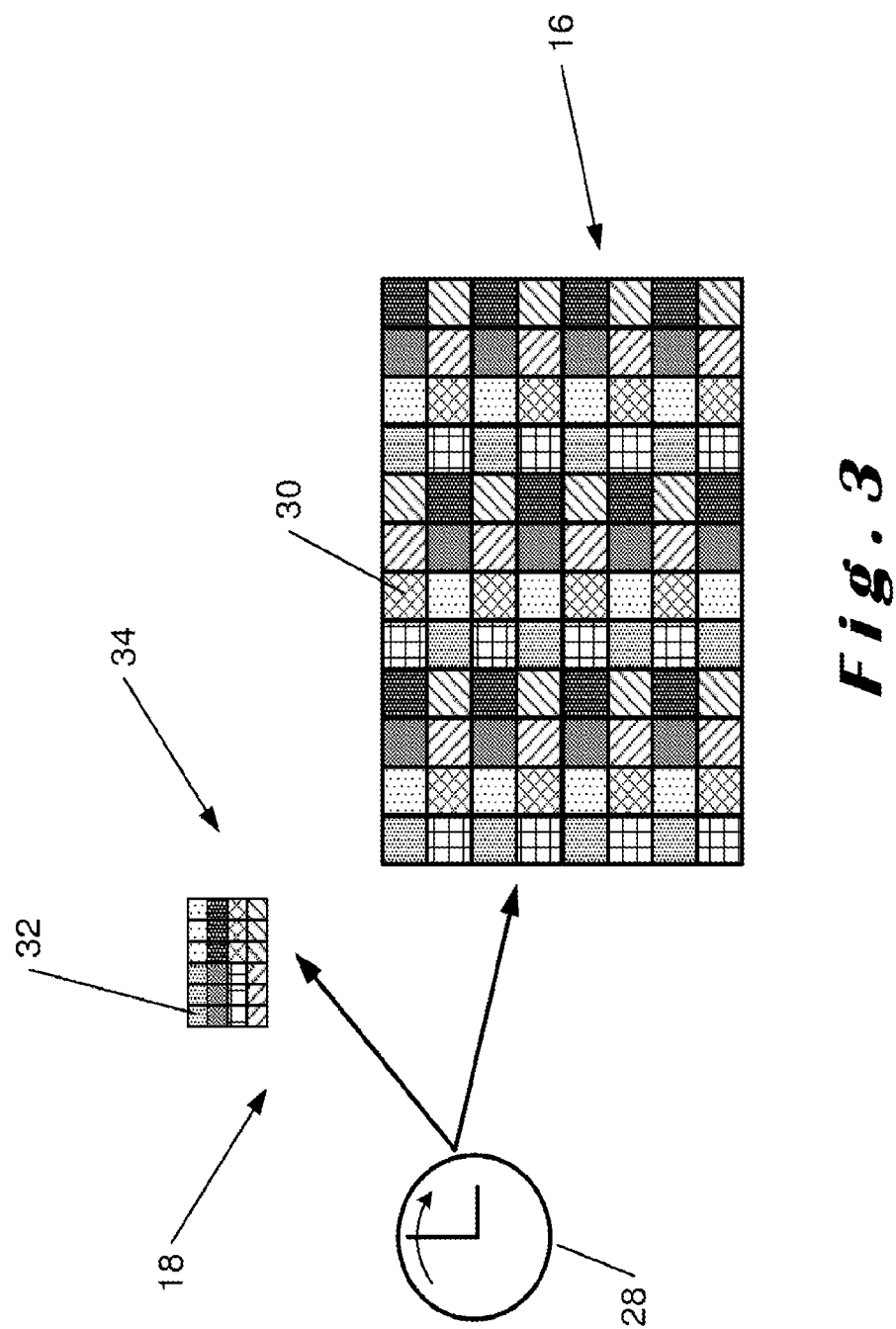
FIG. 3 illustrates a schematic view of the operation of the system according to the invention in another example.

FIGS. 2 and 3 show an example of how the disclosure works. In FIGS. 2 and 3, a sensor 18 is used in the form of a camera 18. The display on the camera 18 and the screen 16 scans from left to right and top to bottom.

FIG. 2 shows the relationship between the pixels 32 of the camera 18 and the pixels 30 of the screen 16 capturing the subject's reactions. The graphical correspondence represents the pixels that are acquired when one of the images of the stimuli is presented. The logic unit 20 commands the refresh and capture frequencies so that they are a multiple of each other. In this example, the central unit 20 commands the frequency of the camera 18 to a higher value; over the time that an image is displayed on the screen 16, the sensor 18 in the form of a camera records twelve images 34. In other words, for every eight pixels 30 refreshed on the screen 16, the camera 18 captures an image 34. For each series of eight pixels 30 refreshed on the screen 16, the camera 18 captures an image 34—i.e., twelve images 34. In addition, the clock 28 commands the triggering of the refresh of the pixels 30 of the screen 16 and of the capture of the images 34 by the camera 18. The presentation of the first pixel of the screen 16 begins at the same time as the capture of the first pixel of the first image from the camera 18. Thus, as a result of the frequencies that are multiples of each other, the first image 34 from the camera 18 is acquired when the first eight pixels 30 of the screen 16 are displayed, and so on. In the example shown in FIG. 2, the screen 16 has a refresh frequency of 1 and the camera 18 has a capture frequency of 12. There is therefore a bijective relationship between the moment when a pixel 32 on the camera 18 is acquired and a pixel 30 on the screen 16 is displayed or refreshed. One therefore obtains a synchronisation of the value of the frequencies and of the phase of the triggering of the refresh and of the capture.

FIG. 3 shows in more detail the relationship between the pixels 32 of the camera 18 and the pixels 30 of the screen 16, with different frequencies. The graphical correspondence represents the pixels that are acquired when one of the images of the stimuli is presented. The logic unit 20 commands the refresh and capture frequencies so that they are a multiple of each other. In this example, the central unit 20 commands the frequency of the camera 18 to a higher value; over the time that a pixel 30 is displayed by the screen 16, the sensor 18 in the form of a camera records three pixels in the image 34. In addition, the clock 28 commands the triggering of the refresh of the pixels 30 of the screen 16 and of the capture of the image 34 by the camera 18. The presentation of the first pixel of the screen 16 begins at the same time as the capture of the first pixel of the first image from the camera 18. Thus, as a result of the frequencies that are multiples of each other, the first three pixels 32 of the camera 18 are acquired when the first pixel 30 of the screen 16 is displayed, and so on. In the example shown in FIG. 3, the screen 16 has a refresh frequency of 1 and the camera 18 has a capture frequency of 12. There is therefore a bijective relationship between the moment when a pixel 32 on the camera 18 is acquired and a pixel 30 on the screen 16 is displayed or refreshed. One therefore obtains a synchronisation of the value of the frequencies and of the phase of the triggering of the refresh and of the capture.

In this way, the system and the method of the disclosure allow to obtain information linked and determined by the display mode via the screen and the capture mode via the sensor or the sensors. Thanks to the logic unit and the central clock—and their respective uniqueness-commanding the frequencies and the triggering of the refresh and of the capture, it is possible to conclude which pixel is being presented at a given moment and to be able to conclude which part of the image is being acquired at that moment.

The disclosure also proposes a computer program comprising instructions which, when the computer program is executed by a computer, cause the system 12 to execute the steps of the method according to any one of the embodiments of the disclosure.

Finally, the disclosure also proposes a computer-readable medium on which the above-mentioned computer program is recorded. The computer-readable medium preferably consists of at least one computer medium (or a set of such media) capable of storing digital information. It comprises, for example, at least one of the following: a digital memory, a server, a USB key or a computer. It can be in a cloud.

By using the term "computer", the disclosure implies the use of a computer, a computer network and/or any other programmable apparatus (for example, a smartphone, a tablet, etc.). In particular, the term "computer" cannot be interpreted restrictively.

The present disclosure has been described above in connection with specific embodiments, which are illustrative and should not be considered limiting. Generally speaking, it will be obvious to a person skilled in the art that the present disclosure is not limited to the examples illustrated and/or described above.

What is claimed is:

1. A system for measuring reactions of a subject, comprising:
   a screen capable of displaying a plurality of stimuli via a refresh of pixels of the screen, the stimuli being capable of generating reactions from the subject;
   at least one sensor capable of capturing images of the subject in reaction to the stimuli; and
   a logic unit configured to command the refresh of the pixels of the screen at a first frequency and the capture of the images of the subject by the at least one sensor at a second frequency, one of the frequencies being an integer multiple of the other frequency, the logic unit comprising a central clock configured to command simultaneous triggering of the refresh of pixels of the screen and the capture of the images at one or more edges of the central clock,
   wherein there is a bijective relationship between a moment at which a pixel on the sensor is acquired and a moment at which a pixel on the screen is refreshed based on the simultaneous triggering of the refresh of pixels of the screen and the capture of the images.

2. The system according to claim 1, wherein the integer multiple is 1 and the logic unit is configured to command the refresh of the pixels of the screen and the capture of the images of the subject by the at least one sensor at the same frequency.

3. The system according to claim 1, wherein the first frequency is faster than the second frequency, the first frequency being an integer multiple of the second frequency.

4. The system according to claim 1, wherein the second frequency is faster than the first frequency, the second frequency being an integer multiple of the first frequency.

5. The system according to claim 1, wherein
   the command of the frequencies for the refresh of the pixels of the screen and for the capture of the images by the at least one sensor is performed solely by the logic unit, and
   the command of the refresh of the pixels of the screen and of the capture of the images by the at least one sensor is performed solely by the central clock of the logic unit.

6. The system according to claim 1, wherein the logic unit is connected directly to the screen and to the at least one sensor.

7. The system according to claim 1, wherein the images captured by the at least one sensor are images of at least one eye of the subject.

8. The system according to claim 1, wherein the at least one sensor comprises two sensors in the form of cameras, each sensor capturing images of a respective eye of the subject.

9. The system according to claim 1, wherein the at least one sensor and the screen are scanned from left to right and top to bottom.

10. A method for measuring reactions of a subject, comprising the following steps:
    providing a screen, at least one sensor, and a logic unit comprising a central clock; and
    displaying by the screen a plurality of stimuli by a refresh of pixels of the screen, the stimuli generating reactions from the subject, and capturing, by the at least one sensor, images of the subject in reaction to the stimuli;
    wherein the refresh of the pixels of the screen and the capture of the images of the subject by the at least one sensor being commanded by the logic unit respectively at a first frequency and a second frequency, one of the frequencies being an integer multiple of the other frequency, and the central clock is configured to command simultaneous triggering of the refresh of pixels of the screen and the capture of the images by the at least one sensor at one or more edges of the central clock, and
    wherein there is a bijective relationship between a moment at which a pixel on the sensor is acquired and a moment at which a pixel on the screen is refreshed based on the simultaneous triggering of the refresh of pixels of the screen and the capture of the images.

11. The method according to claim 10, wherein the integer multiple is 1, the logic unit commanding the refresh of the pixels of the screen and the capture of the images of the subject by the at least one sensor at the same frequency.

12. The method of claim 10, wherein the first frequency is faster than the second frequency, the first frequency being an integer multiple of the second frequency.

13. The method of claim 10, wherein the second frequency is faster than the first frequency, the second frequency being an integer multiple of the first frequency.

14. The method of claim 10, wherein the at least one sensor comprises two sensors, and wherein:
the providing step comprises providing the two sensors in the form of cameras; and
the capturing step comprises the capture by each sensor of images of a respective eye of the subject.

15. A computer program comprising instructions that cause a system for measuring reactions of a subject to execute the method of claim 10,
wherein the screen is capable of displaying a plurality of stimuli via a refresh of pixels of the screen, the stimuli being capable of generating reactions from the subject, the at least one sensor capable of capturing images of the subject in reaction to the stimuli, a logic unit configured to command the refresh of the pixels of the screen at a first frequency and the capture of the images of the subject by the at least one sensor at a second frequency, one of the frequencies being an integer multiple of the other frequency, the logic unit comprising a central clock configured to command the refresh of pixels of the screen and the capture of the images.

16. A non-transitory computer-readable storage medium having program instructions recorded thereon that, when executed by at least one processing circuit of a computing device, perform a method for measuring reactions of a subject, comprising:
providing a screen, at least one sensor, and a logic unit comprising a central clock; and
displaying by the screen a plurality of stimuli by a refresh of pixels of the screen, the stimuli generating reactions from the subject, and capturing, by the at least one sensor, images of the subject in reaction to the stimuli,
wherein the refresh of the pixels of the screen and the capture of the images of the subject by the at least one sensor being commanded by the logic unit respectively at a first frequency and a second frequency, one of the frequencies being an integer multiple of the other frequency, and the central clock is configured to command simultaneous triggering of the refresh of pixels of the screen and the capture of the images by the at least one sensor at one or more edges of the central clock,
wherein there is a bijective relationship between a moment at which a pixel on the sensor is acquired and a moment at which a pixel on the screen is refreshed based on the simultaneous triggering of the refresh of pixels of the screen and the capture of the images.

17. The non-transitory computer-readable storage medium according to claim 16, wherein the integer multiple is 1, the logic unit commanding the refresh of the pixels of the screen and the capture of the images of the subject by the at least one sensor at the same frequency.

18. The non-transitory computer-readable storage medium according to claim 16, wherein the first frequency is faster than the second frequency, the first frequency being an integer multiple of the second frequency.

19. The non-transitory computer-readable storage medium according to claim 16, wherein the second frequency is faster than the first frequency, the second frequency being an integer multiple of the first frequency.

20. The non-transitory computer-readable storage medium according to claim 16, wherein the at least one sensor comprises two sensors, and wherein:
the providing step comprises providing the two sensors in the form of cameras; and
the capturing step comprises the capture by each sensor of images of a respective eye of the subject.

* * * * *